(12) United States Patent
Lin

(10) Patent No.: US 12,102,542 B2
(45) Date of Patent: Oct. 1, 2024

(54) INTERSPINOUS SPACER AND METHODS AND SYSTEMS UTILIZING THE INTERSPINOUS SPACER

(71) Applicant: Boston Scientific Neuromodulation Corporation, Valencia, CA (US)

(72) Inventor: Yu-min Lin, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 18/107,376

(22) Filed: Feb. 8, 2023

(65) Prior Publication Data

US 2023/0255786 A1 Aug. 17, 2023

Related U.S. Application Data

(60) Provisional application No. 63/310,449, filed on Feb. 15, 2022.

(51) Int. Cl.
*A61F 2/44* (2006.01)
*A61F 2/46* (2006.01)
*A61F 2/30* (2006.01)

(52) U.S. Cl.
CPC .......... *A61F 2/4405* (2013.01); *A61F 2/4611* (2013.01); *A61F 2002/30405* (2013.01);
(Continued)

(58) Field of Classification Search
None
See application file for complete search history.

(56) References Cited

U.S. PATENT DOCUMENTS 2,248,054 A 7/1941 Becker
2,677,369 A 5/1954 Knowles
(Continued)

FOREIGN PATENT DOCUMENTS

CA 268461 2/1927
CN 2794456 7/2006
(Continued)

OTHER PUBLICATIONS

ASNR Neuroradiology Patient Information website, Brain and Spine Imaging: A Patient's Guide to Neuroradiology; Myelography; http://www.asnr.org/patientinfo/procedures/myelography.shtml#/sthash.sXIDOxWq.dpbs, Copyright 2012-2013.
(Continued)

*Primary Examiner* — Jan Christoher L Merene
(74) *Attorney, Agent, or Firm* — Branch Partners PLLC; Bruce E. Black

(57) ABSTRACT

An interspinous spacer that includes a body having a distal portion and a proximal portion; an actuator at least partially disposed in the body; and a first arm and a second arm, where the first and second arms are rotatably coupled to a distal portion of the body and coupled to the actuator, where the actuator, first arm, and second arm are configured, upon rotation of the actuator in a first direction, to move the first and second arms from an implantation position, in which the first and second arms extend from the distal portion of the body back toward the proximal portion of the body, to a deployed position, in which the first and second arms extend away from the body.

18 Claims, 5 Drawing Sheets

(52) U.S. Cl.
CPC .............. *A61F 2002/3042* (2013.01); *A61F 2002/30528* (2013.01); *A61F 2002/30579* (2013.01)

(56) References Cited

U.S. PATENT DOCUMENTS

| | | |
|---|---|---|
| 2,933,114 A | 4/1960 | Bystrom |
| 3,242,120 A | 3/1966 | Steuber |
| 3,486,505 A | 12/1969 | Morrison |
| 3,648,691 A | 3/1972 | Lumb et al. |
| 3,780,733 A | 12/1973 | Martinez-Manzor |
| 3,986,383 A | 10/1976 | Petteys |
| 4,545,374 A | 10/1985 | Jacobson |
| 4,632,101 A | 12/1986 | Freeland |
| 4,685,447 A | 8/1987 | Iversen et al. |
| 4,799,484 A | 1/1989 | Smith et al. |
| 4,863,476 A | 9/1989 | Sheppard |
| 4,877,020 A | 10/1989 | Vich |
| 4,895,564 A | 1/1990 | Farrell |
| 4,986,831 A | 1/1991 | King et al. |
| 5,011,484 A | 4/1991 | Breard |
| 5,015,247 A | 5/1991 | Michelson |
| 5,019,081 A | 5/1991 | Watanabe |
| 5,040,542 A | 8/1991 | Gray |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,238,295 A * | 8/1993 | Harrell .................. B60N 2/847 297/391 |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville |
| 5,609,636 A | 3/1997 | Kohrs et al. |
| 5,645,599 A | 7/1997 | Samani |
| 5,654,599 A | 8/1997 | Casper |
| 5,658,335 A | 8/1997 | Allen |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura |
| 5,904,636 A | 5/1999 | Chen |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| 6,102,950 A | 8/2000 | Vaccaro |
| D433,193 S | 10/2000 | Gaw et al. |
| 6,132,464 A | 10/2000 | Martin |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,763 B1 | 7/2001 | Castro |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet |
| 6,402,740 B1 | 6/2002 | Ellis et al. |
| 6,402,750 B1 | 6/2002 | Atkinson et al. |
| 6,402,784 B1 | 6/2002 | Wardlaw |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps et al. |
| 6,610,065 B1 | 8/2003 | Branch et al. |
| 6,610,091 B1 | 8/2003 | Reiley |
| 6,616,673 B1 | 9/2003 | Stone et al. |
| 6,626,944 B1 | 9/2003 | Taylor |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |

(56) References Cited

U.S. PATENT DOCUMENTS

| | | |
|---|---|---|
| 6,699,246 B2 | 3/2004 | Zucherman et al. |
| 6,699,247 B2 | 3/2004 | Zucherman et al. |
| 6,702,847 B2 | 3/2004 | Dicarlo |
| 6,712,819 B2 | 3/2004 | Zucherman et al. |
| 6,716,215 B1 | 4/2004 | David et al. |
| 6,716,245 B2 | 4/2004 | Pasquel et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Amin et al. |
| 6,974,478 B2 | 12/2005 | Reiley et al. |
| 6,976,988 B2 | 12/2005 | Ralph et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquel et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,187,064 B2 | 6/2007 | Matge et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Amin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Amin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Amin et al. |
| 7,811,322 B2 | 10/2010 | Amin et al. |
| 7,811,323 B2 | 10/2010 | Amin et al. |
| 7,811,324 B2 | 10/2010 | Amin et al. |
| 7,811,330 B2 | 10/2010 | Amin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Amin et al. |
| 7,837,687 B2 | 11/2010 | Harp |
| 7,837,688 B2 | 11/2010 | Boyer et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 7,985,246 B2 | 7/2011 | Trieu et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |

(56) References Cited

U.S. PATENT DOCUMENTS

| | | |
|---|---|---|
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 9,445,843 B2 | 9/2016 | Altarac et al. |
| 9,532,812 B2 | 1/2017 | Altarac et al. |
| 9,572,603 B2 | 2/2017 | Altarac et al. |
| 9,675,303 B2 | 6/2017 | Choi |
| 9,861,398 B2 | 1/2018 | Altarac et al. |
| 9,956,011 B2 | 5/2018 | Altarac et al. |
| 10,058,358 B2 | 8/2018 | Altarac et al. |
| 10,080,587 B2 | 9/2018 | Altarac et al. |
| 10,166,047 B2 | 1/2019 | Altarac et al. |
| 10,258,479 B2 | 4/2019 | Stewart et al. |
| 10,524,772 B2 | 1/2020 | Choi et al. |
| 10,610,267 B2 | 4/2020 | Altarac et al. |
| 10,653,456 B2 | 5/2020 | Altarac et al. |
| 10,835,295 B2 | 11/2020 | Altarac et al. |
| 10,835,297 B2 | 11/2020 | Altarac et al. |
| 11,013,539 B2 | 5/2021 | Altarac et al. |
| 11,229,461 B2 | 1/2022 | Altarac et al. |
| 2001/0031965 A1 | 10/2001 | Zucherman et al. |
| 2002/0022856 A1 | 2/2002 | Johnson et al. |
| 2002/0042607 A1 | 4/2002 | Palmer et al. |
| 2002/0116009 A1 | 8/2002 | Fraser et al. |
| 2002/0143331 A1 | 10/2002 | Zucherman et al. |
| 2002/0151977 A1 | 10/2002 | Paes et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0105466 A1 | 6/2003 | Ralph et al. |
| 2003/0135275 A1 | 7/2003 | Garcia et al. |
| 2003/0149438 A1 | 8/2003 | Nichols et al. |
| 2003/0153976 A1 | 8/2003 | Cauthen, III et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markwort |
| 2004/0087947 A1 | 5/2004 | Lim et al. |
| 2004/0106997 A1 | 6/2004 | Lieberson |
| 2004/0106999 A1 | 6/2004 | Mathews |
| 2004/0148028 A1 | 7/2004 | Ferree et al. |
| 2004/0167625 A1 | 8/2004 | Beyar et al. |
| 2004/0220568 A1 | 11/2004 | Zucherman et al. |
| 2004/0225295 A1 | 11/2004 | Zubok et al. |
| 2004/0260305 A1 | 12/2004 | Gorensek et al. |
| 2005/0021042 A1 | 1/2005 | Marnay et al. |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0209698 A1 | 9/2005 | Gordon |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0278036 A1 | 12/2005 | Leonard et al. |
| 2006/0030860 A1 | 2/2006 | Peterman |
| 2006/0036258 A1 | 2/2006 | Zucherman et al. |
| 2006/0064107 A1 | 3/2006 | Bertagnoli et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0122458 A1 | 6/2006 | Bleich |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0032790 A1 | 2/2007 | Aschmann et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0073292 A1 | 3/2007 | Kohm et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |

(56) References Cited

U.S. PATENT DOCUMENTS

| | | |
|---|---|---|
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191857 A1 | 8/2007 | Allard et al. |
| 2007/0191948 A1 | 8/2007 | Amin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquel et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276390 A1 | 11/2007 | Salsberg |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0071380 A1 | 3/2008 | Sweeney |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0167657 A1 | 7/2008 | Greenhalgh |
| 2008/0172057 A1 | 7/2008 | Zucherman et al. |
| 2008/0177271 A1 | 7/2008 | Yeh |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0195152 A1* | 8/2008 | Altarac ............... A61B 17/7065 623/17.11 |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0287997 A1 | 11/2008 | Altarac et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2009/0292316 A1* | 11/2009 | Hess ................ A61B 17/7065 606/279 |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |
| 2010/0152775 A1* | 6/2010 | Seifert ............... A61B 17/3468 623/17.11 |
| 2010/0160947 A1 | 6/2010 | Akyuz et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool |
| 2010/0305611 A1 | 12/2010 | Zucherman et al. |

(56) References Cited

U.S. PATENT DOCUMENTS

| | | | |
|---|---|---|---|
| 2011/0172710 A1* | 7/2011 | Thommen | A61B 17/7065 606/249 |
| 2011/0245833 A1 | 10/2011 | Anderson | |
| 2011/0313457 A1 | 12/2011 | Reglos et al. | |
| 2012/0078301 A1 | 3/2012 | Hess | |
| 2012/0158063 A1 | 6/2012 | Altarac et al. | |
| 2012/0226315 A1 | 9/2012 | Altarac et al. | |
| 2012/0232552 A1 | 9/2012 | Morgenstern Lopez et al. | |
| 2012/0303039 A1 | 11/2012 | Chin et al. | |
| 2012/0330359 A1 | 12/2012 | Kim | |
| 2013/0012998 A1 | 1/2013 | Altarac et al. | |
| 2013/0072985 A1 | 3/2013 | Kim | |
| 2013/0165974 A1 | 6/2013 | Kim | |
| 2013/0165975 A1 | 6/2013 | Tebbe et al. | |
| 2013/0172932 A1 | 7/2013 | Altarac et al. | |
| 2013/0172933 A1 | 7/2013 | Altarac et al. | |
| 2013/0289399 A1 | 10/2013 | Choi et al. | |
| 2013/0289622 A1 | 10/2013 | Kim | |
| 2014/0081332 A1 | 3/2014 | Altarac et al. | |
| 2014/0214082 A1 | 7/2014 | Reglos et al. | |
| 2015/0150598 A1 | 6/2015 | Tebbe et al. | |
| 2015/0150604 A1 | 6/2015 | Kim | |
| 2015/0374415 A1 | 12/2015 | Kim | |
| 2016/0030092 A1 | 2/2016 | Altarac et al. | |
| 2016/0066963 A1 | 3/2016 | Kim | |
| 2016/0317193 A1 | 11/2016 | Kim | |
| 2017/0071588 A1 | 3/2017 | Choi et al. | |
| 2017/0128110 A1 | 5/2017 | Altarac et al. | |
| 2017/0156763 A1 | 6/2017 | Altarac et al. | |
| 2017/0245883 A1 | 8/2017 | Tebbe et al. | |
| 2017/0258501 A1 | 9/2017 | Altarac et al. | |
| 2017/0273722 A1 | 9/2017 | Altarac et al. | |
| 2017/0296238 A1 | 10/2017 | Snell et al. | |
| 2017/0348028 A1* | 12/2017 | Calvosa | A61B 17/7067 |
| 2018/0028130 A1 | 2/2018 | Choi | |
| 2018/0193064 A1 | 7/2018 | Kim | |
| 2018/0228519 A1 | 8/2018 | Altarac et al. | |
| 2019/0069933 A1 | 3/2019 | Altarac et al. | |
| 2019/0090912 A1 | 3/2019 | Altarac et al. | |
| 2019/0090913 A1 | 3/2019 | Altarac et al. | |
| 2019/0105082 A1 | 4/2019 | Altarac et al. | |
| 2019/0105083 A1 | 4/2019 | Kim | |
| 2019/0201057 A1 | 7/2019 | Altarac et al. | |
| 2023/0240726 A1* | 8/2023 | Linares | A61B 17/7065 606/249 |

FOREIGN PATENT DOCUMENTS

| | | |
|---|---|---|
| CN | 101897603 | 12/2010 |
| EP | 322334 | 6/1989 |
| EP | 0767636 | 1/1999 |
| EP | 0768843 | 2/1999 |
| EP | 1138268 | 10/2001 |
| EP | 1056408 | 12/2003 |
| EP | 1343424 | 9/2004 |
| EP | 1454589 | 9/2004 |
| EP | 1330987 | 3/2005 |
| EP | 1299042 | 3/2006 |
| EP | 1578314 | 5/2007 |
| EP | 1675535 | 5/2007 |
| EP | 0959792 | 11/2007 |
| EP | 1027004 | 12/2007 |
| EP | 1030615 | 12/2007 |
| EP | 1570793 | 5/2008 |
| EP | 1148850 | 4/2009 |
| EP | 1861046 | 2/2012 |
| FR | 2681525 | 3/1993 |
| FR | 2717675 | 5/1996 |
| FR | 2722980 | 9/1996 |
| FR | 2816197 | 5/2002 |
| SU | 988281 | 1/1983 |
| WO | WO9404088 | 3/1994 |
| WO | WO9426192 | 11/1994 |
| WO | WO9525485 | 9/1995 |
| WO | WO9531158 | 11/1995 |
| WO | WO9600049 | 1/1996 |
| WO | WO9829047 | 7/1998 |
| WO | WO9921500 | 5/1999 |
| WO | WO9921501 | 5/1999 |
| WO | WO9942051 | 8/1999 |
| WO | WO0013619 | 3/2000 |
| WO | WO0044319 | 8/2000 |
| WO | WO0044321 | 8/2000 |
| WO | WO0128442 | 4/2001 |
| WO | WO0191657 | 12/2001 |
| WO | WO0191658 | 12/2001 |
| WO | WO0203882 | 1/2002 |
| WO | WO0207623 | 1/2002 |
| WO | WO0207624 | 1/2002 |
| WO | WO02051326 | 7/2002 |
| WO | WO02067793 | 9/2002 |
| WO | WO02071960 | 9/2002 |
| WO | WO02076336 | 10/2002 |
| WO | WO03007791 | 1/2003 |
| WO | WO03007829 | 1/2003 |
| WO | WO03008016 | 1/2003 |
| WO | WO03015646 | 2/2003 |
| WO | WO03024298 | 3/2003 |
| WO | WO03045262 | 6/2003 |
| WO | WO03099147 | 12/2003 |
| WO | WO03101350 | 12/2003 |
| WO | WO04073533 | 9/2004 |
| WO | WO04110300 | 12/2004 |
| WO | WO05009300 | 2/2005 |
| WO | WO05013839 | 2/2005 |
| WO | WO05025461 | 3/2005 |
| WO | WO05041799 | 5/2005 |
| WO | WO05044152 | 5/2005 |
| WO | WO05055868 | 6/2005 |
| WO | WO05079672 | 9/2005 |
| WO | WO2005086776 | 9/2005 |
| WO | WO05115261 | 12/2005 |
| WO | WO06033659 | 3/2006 |
| WO | WO06034423 | 3/2006 |
| WO | WO06039243 | 4/2006 |
| WO | WO06039260 | 4/2006 |
| WO | WO06045094 | 4/2006 |
| WO | WO06063047 | 6/2006 |
| WO | WO06065774 | 6/2006 |
| WO | WO2006064356 | 6/2006 |
| WO | WO2006089085 | 8/2006 |
| WO | WO06102269 | 9/2006 |
| WO | WO06102428 | 9/2006 |
| WO | WO06102485 | 9/2006 |
| WO | WO06107539 | 10/2006 |
| WO | WO06110462 | 10/2006 |
| WO | WO06110464 | 10/2006 |
| WO | WO06110767 | 10/2006 |
| WO | WO06113080 | 10/2006 |
| WO | WO06113406 | 10/2006 |
| WO | WO06113814 | 10/2006 |
| WO | WO2006106246 | 10/2006 |
| WO | WO06118945 | 11/2006 |
| WO | WO06119235 | 11/2006 |
| WO | WO06119236 | 11/2006 |
| WO | WO06135511 | 12/2006 |
| WO | WO2007010140 | 1/2007 |
| WO | WO07015028 | 2/2007 |
| WO | WO07035120 | 3/2007 |
| WO | WO07075375 | 7/2007 |
| WO | WO07075788 | 7/2007 |
| WO | WO07075791 | 7/2007 |
| WO | WO07089605 | 8/2007 |
| WO | WO07089905 | 8/2007 |
| WO | WO07089975 | 8/2007 |
| WO | WO07097735 | 8/2007 |
| WO | WO07109402 | 9/2007 |
| WO | WO07110604 | 10/2007 |
| WO | WO07111795 | 10/2007 |
| WO | WO07111979 | 10/2007 |
| WO | WO07111999 | 10/2007 |
| WO | WO07117882 | 10/2007 |
| WO | WO07121070 | 10/2007 |

(56) References Cited

FOREIGN PATENT DOCUMENTS

| | | | |
|---|---|---|---|
| WO | WO07127550 | 11/2007 | |
| WO | WO07127588 | 11/2007 | |
| WO | WO07127677 | 11/2007 | |
| WO | WO07127689 | 11/2007 | |
| WO | WO07127694 | 11/2007 | |
| WO | WO07127734 | 11/2007 | |
| WO | WO07127736 | 11/2007 | |
| WO | WO07131165 | 11/2007 | |
| WO | WO07134113 | 11/2007 | |
| WO | WO2008009049 | 1/2008 | |
| WO | WO08048645 | 4/2008 | |
| WO | WO2008057506 | 5/2008 | |
| WO | WO2008130564 | 10/2008 | |
| WO | WO2009014728 | 1/2009 | |
| WO | WO2009033093 | 3/2009 | |
| WO | WO2009083276 | 7/2009 | |
| WO | WO-2009083583 A1 * | 7/2009 | ......... A61B 17/7065 |
| WO | WO2009086010 | 7/2009 | |
| WO | WO2009091922 | 7/2009 | |
| WO | WO2009094463 | 7/2009 | |
| WO | WO2009114479 | 9/2009 | |
| WO | WO2011084477 | 7/2011 | |
| WO | WO2015171814 | 11/2015 | |

OTHER PUBLICATIONS

Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).

Fast, Avital et al., "Surgical Treatment of Lumbar Spinal Stenosis in the Elderly," Arch Phys. Med Rehabil., Mar. 1985, pp. 149-151, vol. 66.

Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).

Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 79-83 (2006).

Mcculloch, John A., Young, Paul H., "Essentials of Spinal Microsurgery," 1998, pp. 453-485. Lippincott-Raven Publishers, Philadelphia, PA (37 pages total).

Minns, R.J., et al., "Preliminary Design and Experimental Studies of a Noval Soft Implant for Correcting Sagittal Plane Instability in the Lumbar Spine," (1997) Spine, 22(16): 1819-1825.

Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.

Swan, Colby, "Point of View: Preliminary Design and Experimental Studies of a Novel Soft Implant for Correcting Sogittal Plane Instability in the Lumbar Spine," Spine, 1997, 22(16), 1826-1827.

Tredway, Trent L. et al., "Minimally Invasive Transforaminal Lumbar Interbody Fusion (MI-TLIF) and Lateral Mass Fusion with the MetRx System," (14 pages total), 2005.

Vaccaro, Alexander J. et al., MasterCases Spine Surgery, 2001, pp. 100-107. Thieme Medical Publishers, Inc., NY. (10 pages total).

Vertos mild Devices Kit—PRT-00430-C—Instructions for Use (13 pages total); see http://vertosmed.com/docs/mild1FU_PRT-00430-C.pdf., 2012.

International Search Report and Written Opinion for PCT Application No. PCT/US2023/012635 mailed Jun. 2, 2023.

* cited by examiner

INTERSPINOUS SPACER AND METHODS AND SYSTEMS UTILIZING THE INTERSPINOUS SPACER

CROSS-REFERENCE TO RELATED APPLICATIONS

This application claims the benefit under 35 U.S.C. § 119(e) of U.S. Provisional Patent Application Ser. No. 63/310,449, filed Feb. 15, 2022, which is incorporated herein by reference.

FIELD

The present invention is directed to the area of interspinous spacers for deployment between adjacent spinous processes. The present invention is also directed to systems and methods for utilizing the interspinous spacer.

BACKGROUND

With spinal stenosis, the spinal canal narrows and pinches the spinal cord and nerves, causing pain in the back and legs. Typically, with age, a person's ligaments may thicken, intervertebral discs may deteriorate, or facet joints may break down. The conditions can contribute to the narrowing of the spinal canal. Injury, heredity, arthritis, changes in blood flow, and other causes may also contribute to spinal stenosis.

Various treatments of the spine have been proposed or used including medications, surgical techniques, and implantable devices that alleviate and substantially reduce pain associated with the back. In one surgical technique, a spacer is implanted between adjacent spinous processes of a patient's spine. The implanted spacer opens the spinal canal, maintains the desired distance between vertebral body segments, and, as a result, avoids or reduces impingement of nerves and relieves pain. For suitable candidates, an implantable interspinous spacer may provide significant benefits in terms of pain relief.

Any surgery is an ordeal. However, the type of device and how it is implanted has an impact. For example, considerations when performing surgery to implant an interspinous spacer include the arrangement of the device and the possibility of damaging bone or tissue.

BRIEF SUMMARY

One aspect is an interspinous spacer that includes a body having a distal portion and a proximal portion; an actuator at least partially disposed in the body; and a first arm and a second arm, where the first and second arms are rotatably coupled to a distal portion of the body and coupled to the actuator, where the actuator, first arm, and second arm are configured, upon rotation of the actuator in a first direction, to move the first and second arms from an implantation position, in which the first and second arms extend from the distal portion of the body back toward the proximal portion of the body, to a deployed position, in which the first and second arms extend away from the body.

In at least some aspects, the body includes a cup and a casing attached to the cup, wherein the actuator includes a head disposed in the cup and a shaft attached to the head and extending through the casing. In at least some aspects, each of the first arm and the second arm are configured for rotation of at least 90 degrees. In at least some aspects, the actuator and each of the first arm and the second arm are configured for rotation in a first direction and then rotation in a second direction opposite the first direction.

In at least some aspects, the interspinous spacer further includes an actuator retainer attached to an end of the shaft of the actuator outside of the casing. In at least some aspects, the head of the actuator includes a shaped cavity configured to receive a shaped spacer engaging bit of a driving tool for rotating the actuator. In at least some aspects, a least a portion of the shaft of the actuator includes threading. In at least some aspects, each of the first arm and the second arm includes an attachment portion with a threaded surface configured for engagement with the threading of the shaft of the actuator. In at least some aspects, each of the attachment portions further includes at least one end stop bounding the threaded surface to resist further rotation of the respective first or second arm. In at least some aspects, at least one of the threading of the shaft of the actuator or the threaded surfaces of the attachment portions of the first and second arms have a mechanical ratio of at least 10:1.

In at least some aspects, the interspinous spacer further includes a first pin rotatably coupling the first arm to the body and a second pin rotatably coupling the second arm to the body. In at least some aspects, the first pin and the second pin are self-locking pins.

Another aspect is a method of using any of the interspinous spacers. The method includes releasably coupling the interspinous spacer in the implantation position to a spacer insertion instrument; inserting the interspinous spacer coupled to the spacer insertion instrument into a patient and between a pair of adjacent spinous processes; rotating the actuator of the interspinous spacer using a driver tool to deploy the first and second arms to the deployed position with each of the arms seating a different one of the adjacent spinous processes; releasing the interspinous spacer from the spacer insertion instrument; and removing the spacer insertion instrument.

A further aspect is an interspinous spacer that includes a body having a distal portion and a proximal portion; an actuator at least partially disposed in the body; and a first arm and a second arm, where the first and second arms are rotatably coupled to the body and coupled to the actuator, where the actuator, first arm, and second arm are configured, upon rotation of the actuator in a first direction, to rotate the first and second arms from an implantation position, in which the first and second arms are disposed adjacent to the body along a majority of a length of each of the first and second arms, to a deployed position, in which the first and second arms extend away from the body.

In at least some aspects, the body includes a cup and a casing attached to the cup, wherein the actuator includes a head disposed in the cup and a shaft attached to the head and extending through the casing. In at least some aspects, the head of the actuator includes a shaped cavity configured to receive a shaped spacer engaging bit of a driving tool for rotating the actuator, wherein a least a portion of the shaft of the actuator includes threading. In at least some aspects, each of the first arm and the second arm includes an attachment portion with a threaded surface configured for engagement with the threading of the shaft of the actuator. In at least some aspects, at least one of the threading of the shaft of the actuator or the threaded surfaces of the attachment portions of the first and second arms have a mechanical ratio of at least 10:1.

Yet another aspect is a method of using any of the interspinous spacers. The method includes releasably coupling the interspinous spacer in the implantation position to a spacer insertion instrument; inserting the interspinous spacer coupled to the spacer insertion instrument into a patient and between a pair of adjacent spinous processes; rotating the actuator of the interspinous spacer using a driver tool to rotate the first and second arms from an implantation position, in which the first and second arms are disposed adjacent to the body along a majority of a length of each of the first and second arms, to a deployed position, in which the first and second arms extend away from the body; releasing the interspinous spacer from the spacer insertion instrument; and removing the spacer insertion instrument.

A further aspect is a kit that includes any of the interspinous spacers; a spacer insertion instrument configured to releasably grip the interspinous spacer for implantation into a patient; and a driver tool including a spacer engaging bit configured to engage the actuator of the interspinous spacer and rotate the actuator by rotation of the driver tool.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of interspinous spacers for deployment between adjacent spinous processes. The present invention is also directed to systems and methods for utilizing the interspinous spacer.

Examples of interspinous spacers are found in U.S. Pat. Nos. 8,123,782; 8,128,662; 8,273,108; 8,277,488; 8,292,922; 8,425,559; 8,613,747; 8,864,828; 9,119,680; 9,155,572; 9,161,783; 9,393,055; 9,532,812; 9,572,603; 9,861,398; 9,956,011; 10,080,587; 10,166,047; 10,610,267; 10,653,456; 10,835,295; 10,835,297; 11,013,539; and 11,229,461, all of which are incorporated herein by reference. (Unless indicated otherwise, the features and methods described in these references can be applied to the interspinous spacers described herein.) In these spacers, the arms typically extend away from the body of the spacer when the spacer is in the implantation position. In these spacers, the arms typically lead the remainder of the spacer when inserted into the body of the patient. During deployment, the arms back toward the body of the spacer and rotate away from the spinal cord to finally be disposed around the adjacent spinous processes.

In contrast, a spacer can include arms that are disposed adjacent the body and extend from the distal portion of the body of the spacer back toward the proximal portion of the body of the spacer when in the implantation position and during implantation. In at least some embodiments, the arms are disposed adjacent to the body along a majority of a length of each of the first and second arms. In at least some embodiments, an end (which may be relatively blunt) of the body of the spacer leads when the spacer is inserted into the body of the patient. In at least some embodiments, leading with a blunt end of the spacer can reduce any likelihood of cutting into bone, ligaments, or other tissue. During deployment, the arms of these spacers rotate in a direction toward the spinal cord and away from the body of the spacer to be finally disposed around the adjacent spinous processes. In at least some embodiments, rotating the arms toward the spinal cord may reduce any likelihood of catching the arms on the spinous processes prior to full deployment.

Figure 1:
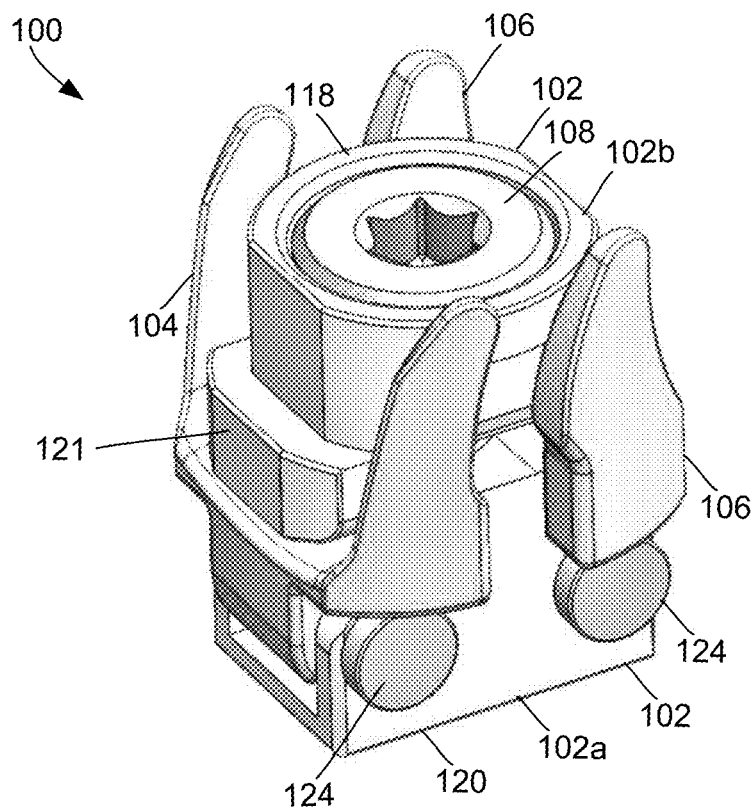
FIG. 1 is a schematic perspective view of one embodiment of an interspinous spacer in an implantation or undeployed position.

FIG. 1 illustrates one embodiment of an interspinous spacer 100 that includes a body 102, a first (or superior) arm 104, a second (or inferior) arm 106, and an actuator 108. The body includes a distal portion 102*a* and a proximal portion 102*b*. The actuator 108 is at least partially disposed in the body 102 and extends from the distal portion 102*a* of the body to the proximal portion 102*b* of the body. The first and second arms 104, 106 are coupled to the distal portion 102*a* of the body 102 and coupled to the actuator 108 for rotation of the arms as described below.

Figure 2:
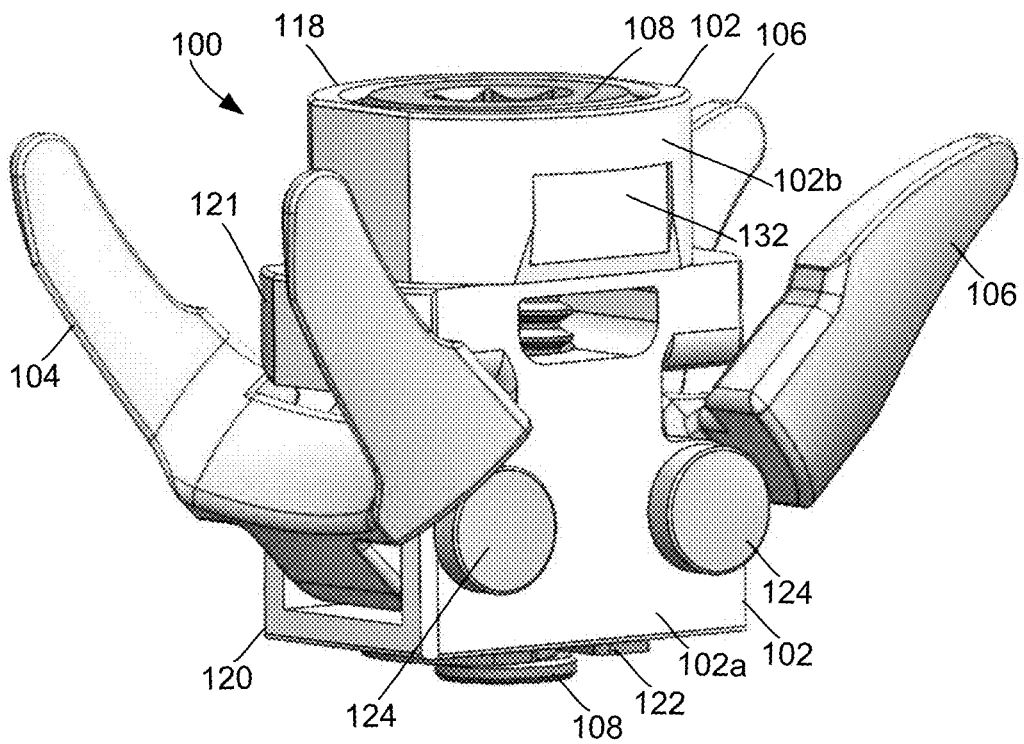
FIG. 2 is a schematic perspective view of the interspinous spacer of FIG. 1 in a partially deployed position.
Figure 4:
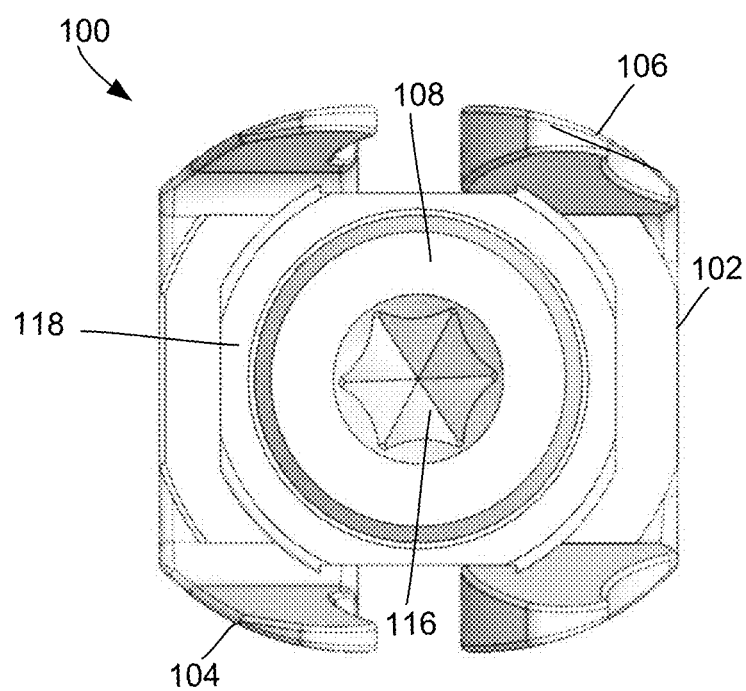
FIG. 4 is a top view of the interspinous spacer of FIG. 1.
Figure 5:
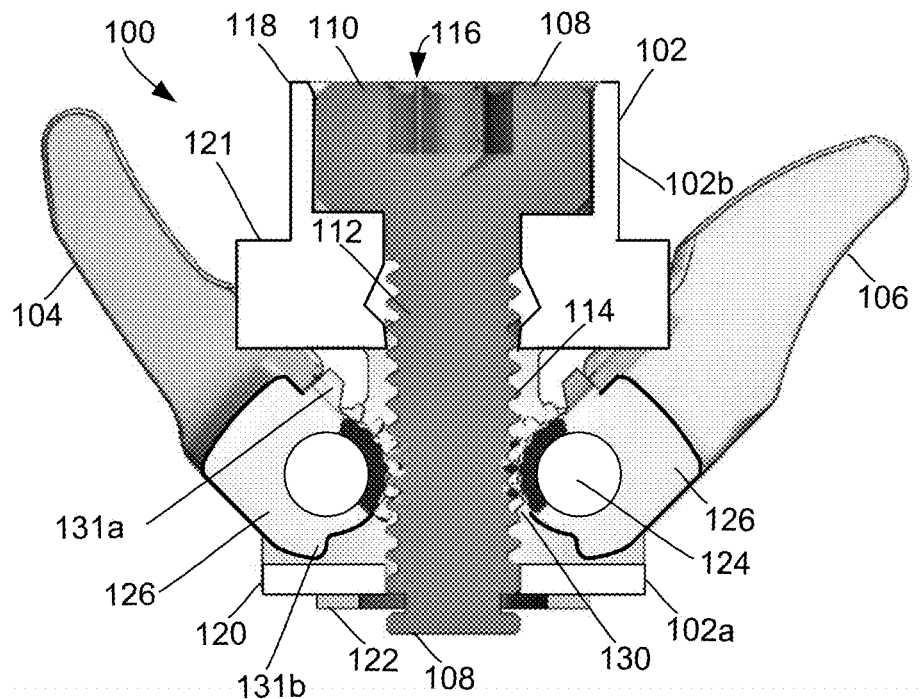
FIG. 5 is a cross-sectional view of at least a portion of the interspinous spacer of FIG. 1.

In FIG. 1, the spacer 100 is in the implantation position (e.g., undeployed position) with the arms 104, 106 extending from the distal portion 102*a* of the body back toward the proximal portion 102*b* of the body and disposed adjacent to the body 102 along at least a majority of the length of the arms, instead of extending away from the body. In FIG. 2, the arms 104, 106 of the spacer 100 are partially deployed and in FIG. 3 the arms 104, 106 are in the deployed position with the arms 104, 106 extending away from the body 102. FIG. 4 is a top view of the spacer, FIG. 5 is a cross-sectional view of at least a portion of the spacer 100, and FIG. 6 is an exploded view of the spacer 100.

Figure 6:
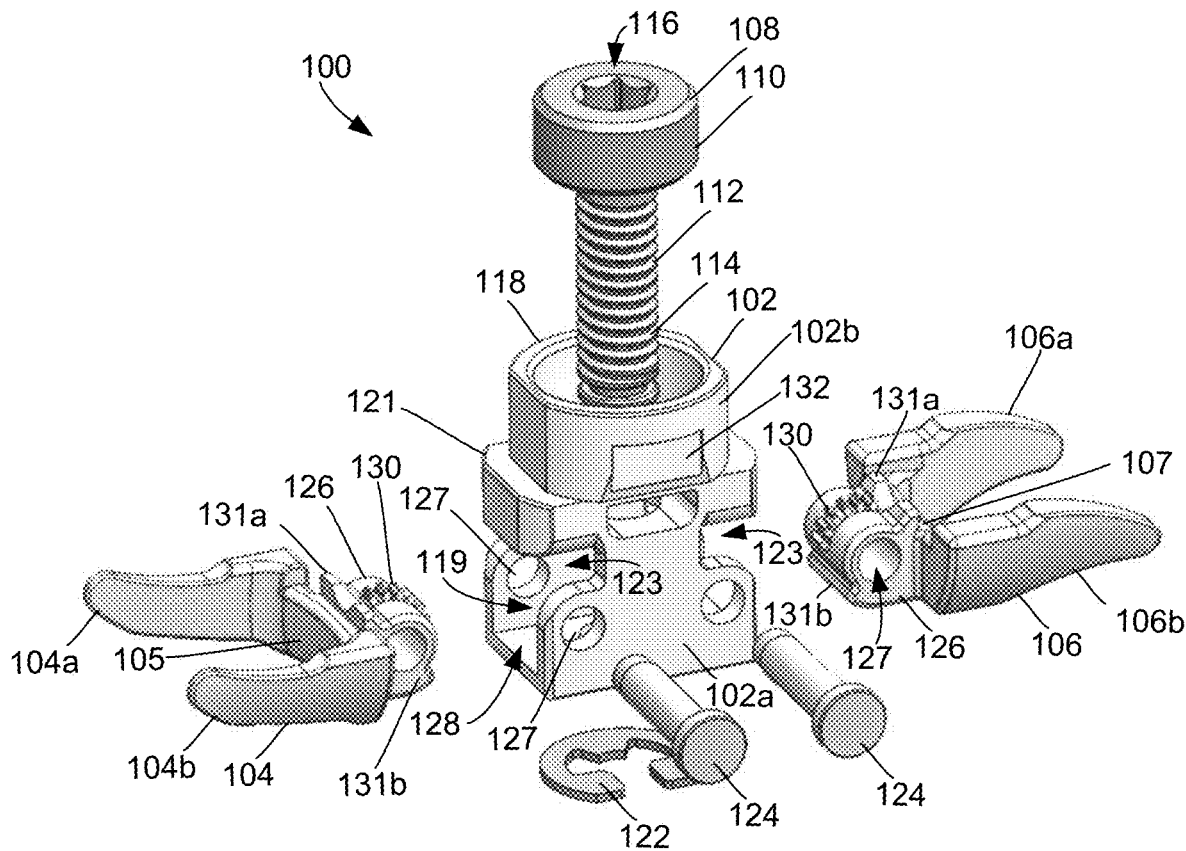
FIG. 6 is an exploded view of the interspinous spacer of FIG. 1.

Turning to FIG. 6, the actuator 108 includes a head 110, a shaft 112 with threads 114 extending along a least a portion of the shaft, and a collar 111 (FIG. 5) and flange 113 (FIG. 5) disposed at an end of the actuator opposite the head. The head 110 of the actuator 108 includes a shaped cavity 116 to receive a driver tool 880 (FIG. 8) with a complementary shaped spacer engaging bit 884. The head 110 of the actuator 108 is disposed in a cup 118 of the body 102 of the spacer 100 and the shaft 112 of the actuator extends into a cavity 119 defined by a casing 120 of the body 102. An actuator retainer 122 is coupled to the collar 111 of the actuator 108 between the flange 113 of the actuator and an outer surface of the casing 120 for retention of the remainder of the actuator in the body 102 of the spacer 100.

The cup 118 is coupled to a proximal end of the casing 120. In at least some embodiments, the cup 118 and casing 120 are formed together by, for example, molding. In other embodiments, the cup 118 is attached to the casing 120 by welding or any other suitable attachment technique. In at least some embodiments, the body 102 includes undercut notches 132 formed on opposite sides of the cup 118. In at least some embodiments, the notches 132 are configured for attachment of clamps 760 of a spacer insertion instrument 750, as described in below with respect to FIG. 7.

Pins 124 extend through pin openings 127 in the casing 120 of the body 120 and attach the arms 104, 106 to the casing. In at least some embodiments, the pins 124 are self-locking pins. Utilizing self-locking pins 124 and a can reduce the need for welding components of the spacer 100.

Each arm 104, 106 includes an attachment portion 126 with a tubular opening 127 for receiving one of the pins 124. Each of the attachment portions 126 extends into the casing 120 through an arm opening 128 in the casing so that each of the arms 104, 106 is rotatably coupled to the body 102 by one of the pins 124.

The arm 104 includes two extensions 104a, 104b coupled by a bridge 105 from which the attachment portion 126 extends. The arm 106 includes two extensions 106a, 106b coupled by a bridge 107 from which the attachment portion 126 extends. In the implantation position (see, FIG. 1), the extensions 104a, 104b, 106a, 106b extend adjacent the body 102 and back toward the cup 118 of the body and, at least in some embodiments, a portion of the extensions 104a, 104b, 106a, 106b extends beyond the cup 118 of the body 102 as illustrated in FIG. 1. In at least some embodiments, in the implantation position, a portion of the body 102 is disposed between extensions 104a, 104b and between extensions 106a, 106b. In at least some embodiments, in the implantation position, at least a portion of the bridges 105, 107 are disposed beneath ledges 121 formed by the casing 120 and cutouts 123 in the casing (see, FIG. 1 for an example of one embodiment of the spacer in the implantation position.) When the arms 104, 106 are deployed, as illustrated in FIG. 3, the pairs of extensions 104a, 140b, 106a, 106b extend away from the body 102 of the spacer 100 with the extensions of each pair disposed on opposing sides of one of the adjacent spinous processes.

Each of the attachment portions 126 of the arms 104, 106 includes a threaded surface 130 that engages (see, FIG. 5) the threads 114 on the shaft 112 of the actuator 108. The threads 114 on the shaft 112 of the actuator 108 act as a track for movement of the arms 104, 106 between the implantation position (FIG. 1) and the deployed position (FIG. 3). As the actuator 108 is rotated in a first direction (for example, clockwise), the arms 104, 106 deploy from the implantation position (see, FIG. 1) to the deployed position (see, FIG. 3). In at least some embodiments, as the actuator 108 is rotated in a second direction (for example, counterclockwise), the arms 104, 106 retract back toward the implantation position. In at least some embodiments, during deployment the arms 104, 106 synchronously deploy opposite each other. During deployment, the arms 104, 106 rotate dorsally and, at least in some embodiments, can cut or dissect tissue from the dorsal direction. In at least some embodiments, the dorsal deployment of the arms 104, 106 of the spacer 100 may be advantageous over the ventral deployment of arms of known spacers. In at least some embodiments, the deployment load is primarily applied by the head 110 of the actuator 108 acting against the cup 118 of the body 102.

Figure 3:
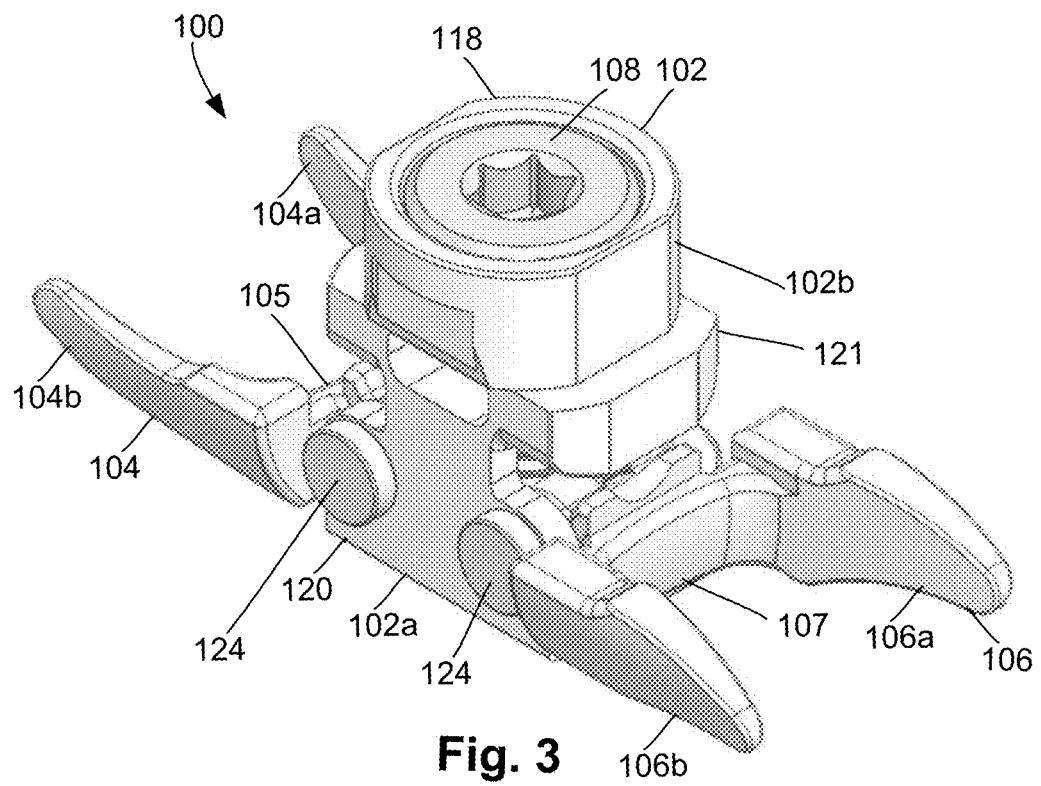
FIG. 3 is a schematic perspective view of the interspinous spacer of FIG. 1 in a deployed position.

In at least some embodiments, during deployment, the arms 104, 106 rotate through an arc of approximately 90 degrees with respect to the body 102 to the deployed position in which the extensions 104a, 104b, 106a, 106b of the arms are approximately perpendicular to the longitudinal axis of the body 102 as shown in FIG. 3. In at least some embodiments, the arms 104, 106 have a U-shaped projection in a plane perpendicular to the longitudinal axis of the body 102.

In at least some embodiments, the threaded surface 130 on the attachment portions 126 of each of the arms 104, 106 is bounded by one or more end stops 131a, 131b (FIG. 5) that preclude further rotation of the arms 104, 106. In at least some embodiments, the threaded surface 130 on the attachment portions 126 of each of the arms 104, 106 or the threads 114 on the shaft 112 of the actuator 108 (or any combination thereof) are selected to have a mechanical ratio (for example, a mechanical ratio of at least 10:1, 15:1, 20:1, 25:1, or more) that resists or prevents rotation of the arms 104, 106 by application of pressure or force against the arms. This can, for example, prevent or resist force applied to the arms by movement or the like from inadvertently rotating the arms 104, 106 after deployment.

In at least some embodiments, the length of the bridge 105 of the arm 104 is approximately 7 to 10 millimeters and the length of the bridge 107 of the arm 106 is approximately 5 to 8 millimeters. In at least some embodiments, the tip-to-tip distance of the extensions 104a, 104b is approximately 8 to 12 millimeters and the tip-to-tip distance of the extensions 106a, 106b is approximately 8 to 12 millimeters. In at least some embodiments, the arm 104 forms a larger space for receiving the superior spinous process than the space formed by the arm 106 for receiving the inferior spinous processes as spinous processes are naturally narrower on top and wider on the bottom.

U.S. Pat. Nos. 8,123,782; 8,128,662; 8,273,108; 8,277,488; 8,292,922; 8,425,559; 8,613,747; 8,864,828; 8,945,183; 9,119,680; 9,155,572; 9,161,783; 9,393,055; 9,532,812; 9,572,603; 9,861,398; 9,956,011; 10,080,587; 10,166,047; 10,610,267; 10,653,456; 10,835,295; 10,835,297; 11,013,539; and 11,229,461, all of which are incorporated herein by reference, illustrate a variety of tools for insertion and deployment of a spacer between adjacent spinous processes. These tools can be used or modified for insertion and deployment of the spacer 100 described above.

Figure 7:
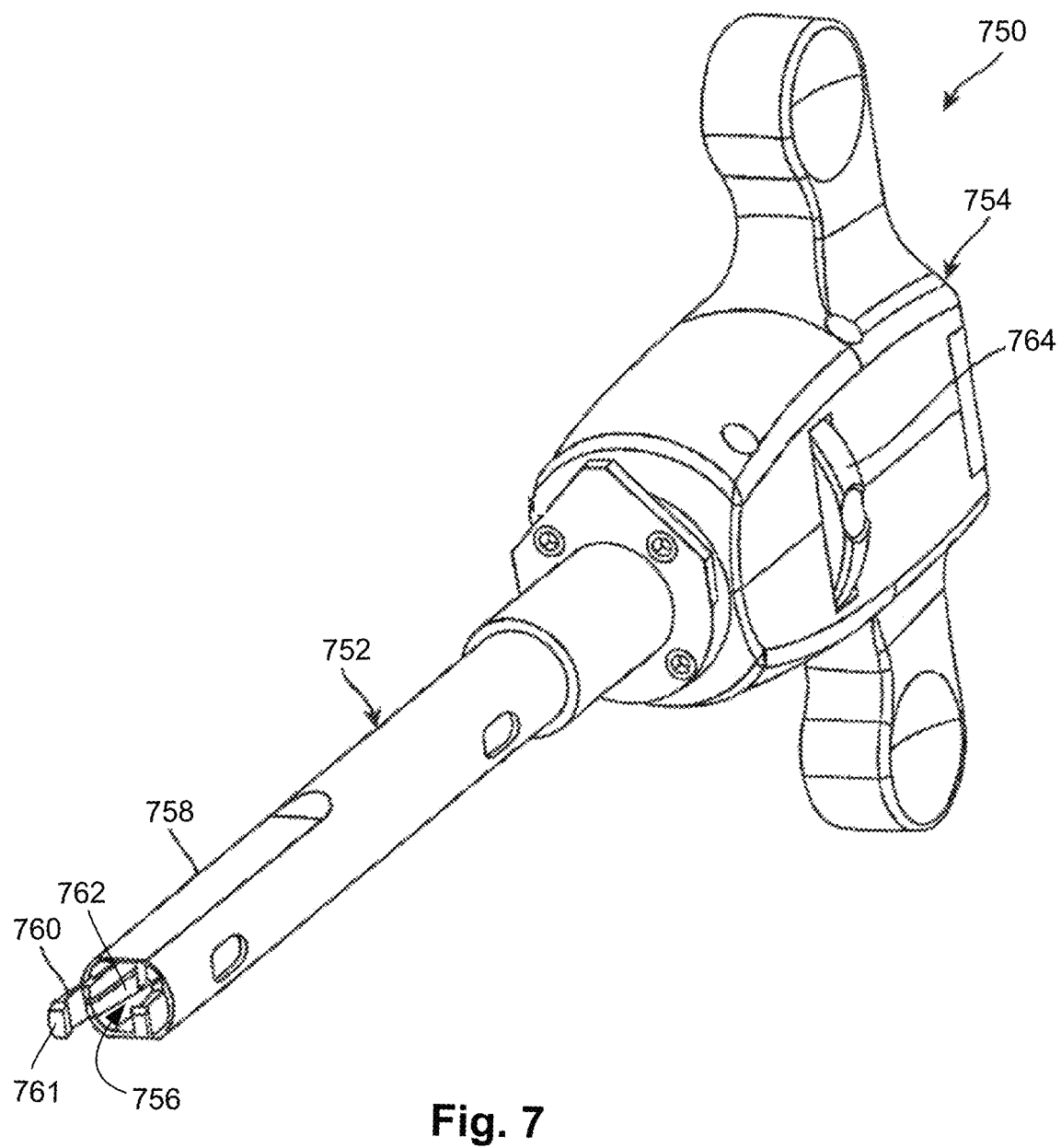
FIG. 7 is a perspective view of one embodiment of a spacer insertion instrument.
Figure 8:
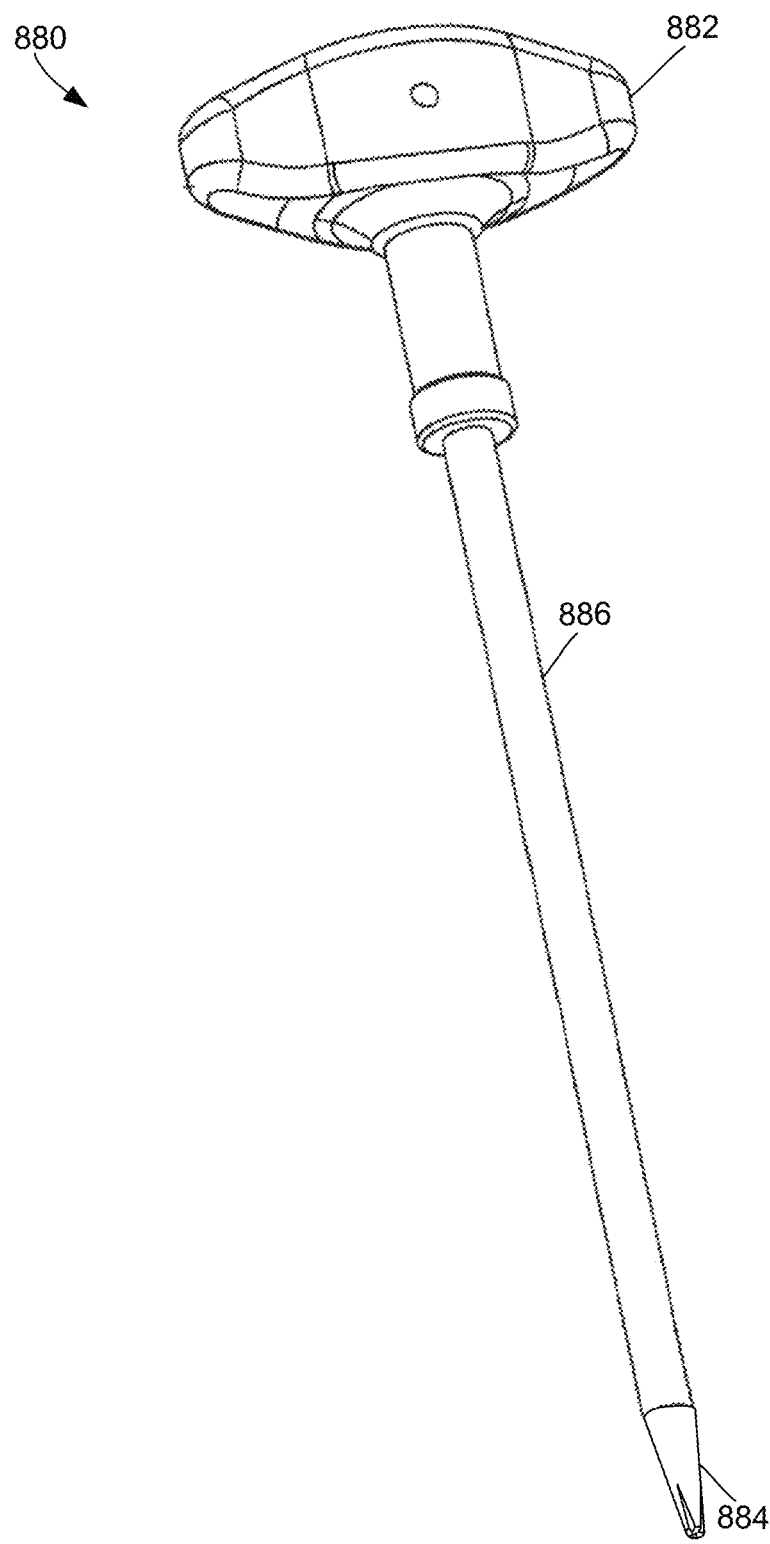
FIG. 8 is a perspective view of one embodiment of a driver tool.

As an example, FIGS. 7 and 8 illustrate a spacer insertion instrument 750 and a driver tool 880, respectively. The spacer insertion instrument 750 includes a cannula 752 connected to a handle 754. The spacer insertion instrument 750 defines a central passageway 756 through the handle 754 and cannula 752. The driver tool 880 is removably insertable into the central passageway 756.

The cannula 752 includes clamps (for example, prongs) 760 to releasably clamp to the body 102 of the spacer 100 (for example, to the undercut notches 132 formed on opposite sides of the cup 118 of the body) for delivery of the spacer into the patient using the pacer insertion instrument 750. In at least some embodiments, the clamps 760 include extensions 761 that extend inwardly toward each other to form hooks. In at least some embodiments, the extensions 761 can engage the undercut notches 132 (FIG. 6) formed on opposite sides of the cup 118 of the body 102 of the spacer 100 to grip the spacer.

The cannula 752 also includes an inner shaft 762 (to which the clamps 760 are attached), an outer shaft 758, and a control 764. In at least some embodiments, the inner shaft 762 is connected to the handle 754 and the outer shaft 758 is passed over the inner shaft 762.

The outer shaft 758 translates with respect to the inner shaft 762 (or, alternatively, the inner shaft translates with respect to the outer shaft) using the control 764. The translation of the outer shaft 758 (or the inner shaft 762) operates the clamps 760. When the outer shaft 758 moves away from the clamps 760, the clamps separate to allow loading (or unloading) of the spacer 100 on the spacer insertion instrument 750. When the outer shaft 758 moves toward the clamps 760, the clamps are moved together to grip the spacer 100. For example, the clamps 760 can grip the undercut notches 132 formed on opposite sides of the cup 118 of the body 102 of the spacer 100. In this manner, the spacer insertion instrument 750 can hold the spacer 100 for delivery of the spacer into position between adjacent spinous processes within the patient.

Turning to FIG. 8, a driver tool 880 includes a handle 882 at the proximal end and a spacer engaging bit 884 at the distal end. The handle 882 and spacer engaging bit 884 are connected by a shaft 886. The driver tool 880 is sized to be inserted into the central passageway 756 of the spacer insertion instrument 750 such that the spacer engaging bit 884 at the distal end operatively connects with a spacer 100 gripped by the clamps 760 of the spacer insertion instrument 750. The spacer engaging bit 884 includes features for engaging with the shaped cavity 116 (see, FIG. 6) in the head 110 of the actuator 108 of the spacer 100. In at least some embodiments, the driver tool 880 has a spacer engaging bit 884 that is complementary to the shaped cavity 116 in the head 110 of the actuator 108 of the spacer 100. Rotating the driver tool 880 when engaged with the head 110 of the spacer 100 rotates the actuator 108 to deploy the arms 104, 106 of the spacer (or, in at least some embodiments, return the arms to the implantation position if rotated in the opposite direction.)

In at least some embodiments, a small midline or lateral-to-midline incision is made in the patient for percutaneous delivery of the spacer 100. In at least some embodiments, the supraspinous ligament is avoided. In at least some embodiments, the supraspinous ligament is split longitudinally along the direction of the tissue fibers to create an opening for the instrument. In at least some embodiments, one or more dilators may be used to create or enlarge the opening.

In at least some embodiments, the spacer 100, in the implantation state (see, FIG. 1), is releasably attached to the spacer insertion instrument 750 as described above. In at least some embodiments, the spacer 100 is inserted into a port or cannula, if one is employed, which has been operatively positioned to form an opening to the interspinous space within a patient's back. The spacer 100, attached to the spacer insertion instrument 750, is inserted into the interspinous space between the spinous processes of two adjacent vertebral bodies. In at least some embodiments, the spacer 100 is advanced beyond the end of a cannula or, alternatively, the cannula is pulled proximately to uncover the spacer 100 connected to the spacer insertion instrument 750. Once in position, the driver tool 880 is inserted into the spacer insertion instrument 750, if not previously inserted, to engage the actuator 108. The driver tool 880 is rotated to rotate the actuator 108. The rotating actuator 108 begins deployment of the arms 104, 106 of the spacer 100. Rotation in one direction, for example, clockwise, for example, deploys the arms 104, 106 through a partially deployed position (see, FIG. 2) to the deployed position (see, FIG. 3).

Other than the implantation position or deployed position, the arms 104, 106 of the spacer may be positioned in one of many partially deployed positions or intermediary positions. In at least some, embodiments, the deployment of the arms 104, 106 can be reversed by rotating the actuator 108 in the opposite direction, for example, counterclockwise.

In at least some embodiments, a clinician can observe with fluoroscopy or other imaging technique the positioning of the spacer 100 inside the patient and then choose to reposition the spacer 100 if desired. Repositioning of the spacer may involve reversing, or partially reversing, the deployment of the arms 104, 106. The arms 104, 106 of the spacer 100 may then be re-deployed into the desired location. This process can be repeated as necessary until the clinician has achieved the desired positioning of the spacer in the patient.

Following deployment of the spacer, the, the spacer insertion instrument 750 and driver tool 880 (and any other instrumentation, such as a cannula or dilator) is removed from the body of the patient. The spacer insertion instrument 750 can be operated as described above to release the clamps 760 from the spacer 100.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An interspinous spacer, comprising:
a body having a first pair of opposing, lateral, external sides, a second pair of opposing, lateral, external sides different from the first pair, a distal portion, and a proximal portion, wherein the body defines an opening on each side of the first pair of opposing, lateral, external sides;
an actuator at least partially disposed in the body;
a first arm and a second arm, wherein each of the first arm and the second arm comprises two extensions, a bridge coupling the two extensions together, and an attachment portion extending from the bridge, through the opening of a one of the sides of the first pair of opposing, lateral, external sides, toward the actuator, wherein the attachment portion is rotatably coupled to the body and engages the actuator, wherein the actuator, first arm, and second arm are configured, upon rotation of the actuator in a first direction, to rotate the first and second arms from an implantation position, in which the two extensions of each of the first arm and the second arm are external to a remainder of the interspinous spacer with a portion of each sides of the second pair of opposing, external, lateral sides of the body between the two extensions along a majority of a length of the two extensions, to a deployed position, in which the first and second arms extend away from the body;
a first pin rotatably coupling the first arm to the body; and
a second pin rotatably coupling the second arm to the body.

2. The interspinous spacer of claim 1, wherein the body comprises a cup and a casing attached to the cup, wherein the actuator comprises a head disposed in the cup and a shaft attached to the head and extending through the casing.

3. The interspinous spacer of claim 2, wherein the head of the actuator comprises a shaped cavity configured to receive a shaped spacer engaging bit of a driving tool for rotating the actuator, wherein a least a portion of the shaft of the actuator comprises threading.

4. The interspinous spacer of claim 3, wherein the attachment portion of each of the first arm and the second arm comprises a threaded surface configured for engagement with the threading of the shaft of the actuator.

5. The interspinous spacer of claim 2, further comprising an actuator retainer attached to an end of the shaft of the actuator outside of the casing.

6. The interspinous spacer of claim 2, wherein a least a portion of the shaft of the actuator comprises threading.

7. The interspinous spacer of claim 6, wherein the attachment portion of each of the first arm and the second arm comprises a threaded surface configured for engagement with the threading of the shaft of the actuator.

8. The interspinous spacer of claim 7, wherein each of the attachment portions further comprises at least one end stop bounding the threaded surface to resist further rotation of the respective first or second arm.

9. The interspinous spacer of claim 1, wherein, in the deployed position, the first arm is configured for receiving a first spinous process between the two extensions with the two extensions disposed on opposing sides of the first spinous process and the second arm is configured for receiving a second spinous process between the two extensions with the two extensions disposed on opposing sides of the second spinous process when the body is disposed between the first and second spinous processes.

10. The interspinous spacer of claim 1, wherein the first pin and the second pin are self-locking pins.

11. The interspinous spacer of claim 1, wherein
the first pin is positioned between the actuator and the bridge of the first arm and
the second pin is positioned between the actuator and the bridge of the second arm.

12. The interspinous spacer of claim 11, wherein the body comprises a cup and a casing attached to the cup, wherein the actuator comprises a head disposed in the cup and a shaft attached to the head and extending through the casing.

13. The interspinous spacer of claim 12, wherein the head of the actuator comprises a shaped cavity configured to receive a shaped spacer engaging bit of a driving tool for rotating the actuator.

14. The interspinous spacer of claim 1, wherein each of the first arm and the second arm are configured for rotation of at least 90 degrees.

15. The interspinous spacer of claim 1, wherein the actuator and each of the first arm and the second arm are configured for rotation in a first direction and then rotation in a second direction opposite the first direction.

16. The interspinous spacer of claim 11, wherein the first pin and the second pin are self-locking pins.

17. A method of using the interspinous spacer of claim 1, the method comprising;
releasably coupling the interspinous spacer in the implantation position to a spacer insertion instrument;
inserting the interspinous spacer coupled to the spacer insertion instrument into a patient and between a pair of adjacent spinous processes;
rotating the actuator of the interspinous spacer using a driver tool to rotate the first and second arms from an implantation position, in which the first and second arms are disposed adjacent to the body along a majority of a length of each of the first and second arms, to a deployed position, in which the first and second arms extend away from the body;
releasing the interspinous spacer from the spacer insertion instrument; and
removing the spacer insertion instrument.

18. A kit, comprising:
the interspinous spacer of claim 1;
a spacer insertion instrument configured to releasably grip the interspinous spacer for implantation into a patient; and
a driver tool comprising a spacer engaging bit configured to engage the actuator of the interspinous spacer and rotate the actuator by rotation of the driver tool.

* * * * *